(12) United States Patent
Kato

(10) Patent No.: US 11,197,723 B2
(45) Date of Patent: Dec. 14, 2021

(54) MEDICAL GUIDANCE SYSTEM AND METHOD USING LOCALIZED INSERTION PLANE

(71) Applicant: Canon USA Inc., Melville, NY (US)

(72) Inventor: Takahisa Kato, Brookline, MA (US)

(73) Assignee: Canon U.S.A., Inc., Melville, NY (US)

(\*) Notice: Subject to any disclaimer, the term of this patent is extended or adjusted under 35 U.S.C. 154(b) by 922 days.

(21) Appl. No.: 15/727,978

(22) Filed: Oct. 9, 2017

(65) Prior Publication Data

US 2019/0105109 A1 Apr. 11, 2019

(51) Int. Cl.
| | |
|---|---|
| *A61B 34/20* | (2016.01) |
| *A61B 34/10* | (2016.01) |
| *A61B 6/03* | (2006.01) |
| *A61B 90/00* | (2016.01) |
| *G16H 40/63* | (2018.01) |
| *A61B 34/00* | (2016.01) |
| *A61B 90/11* | (2016.01) |

(52) U.S. Cl.
CPC ............. *A61B 34/20* (2016.02); *A61B 6/032* (2013.01); *A61B 34/00* (2016.02); *A61B 34/10* (2016.02); *A61B 90/11* (2016.02); *A61B 90/39* (2016.02); *G16H 40/63* (2018.01); *A61B 2034/107* (2016.02); *A61B 2034/2046* (2016.02); *A61B 2034/2059* (2016.02); *A61B 2034/2065* (2016.02); *A61B 2090/3966* (2016.02); *A61B 2090/3983* (2016.02); *A61B 2090/3991* (2016.02)

(58) Field of Classification Search
None
See application file for complete search history.

(56) References Cited

U.S. PATENT DOCUMENTS

| | | |
|---|---|---|
| 5,196,019 A | 3/1993 | Davis et al. |
| 5,957,934 A | 9/1999 | Rapoport |
| 6,119,032 A | 9/2000 | Martin et al. |
| 6,185,445 B1 | 2/2001 | Knuttel |
| 6,487,431 B1 | 11/2002 | Iwano et al. |

(Continued)

FOREIGN PATENT DOCUMENTS

| | | |
|---|---|---|
| JP | H11-155881 A | 6/1999 |
| JP | 2007-527729 A | 10/2007 |

(Continued)

*Primary Examiner* — Luther Behringer
(74) *Attorney, Agent, or Firm* — Canon U.S.A., Inc., IP Division

(57) ABSTRACT

A system and method configured to position medical instruments. The system and method includes an orientation localizer including at least one fiducial marker and having a localized plane, wherein the orientation localizer is mountable at a skin entry point on a patient, a computer configured to receive at least one medical image on the localized plane, register a position and orientation of the orientation localizer with the at least one medical image using the at least one fiducial marker, determine at least one cross sectional image based on the at least one medical image on the localized plane, and determine an insertion plane perpendicular to the localized plane, and an image display connected to the computer, wherein the image display displays the at least one cross sectional image on the localized plane and/or on the insertion plane.

20 Claims, 14 Drawing Sheets

(56) References Cited

U.S. PATENT DOCUMENTS

| | | | |
|---|---|---|---|
| 6,505,065 | B1 | 1/2003 | Yanof et al. |
| 7,083,608 | B2 | 8/2006 | Tomita et al. |
| 7,187,104 | B2 | 3/2007 | Yamamoto et al. |
| 7,824,417 | B2 | 11/2010 | Magnusson et al. |
| 7,876,942 | B2 * | 1/2011 | Gilboa .................. A61B 34/20 |
| | | | 382/128 |
| 8,308,740 | B2 | 11/2012 | Tolley et al. |
| 8,511,316 | B2 | 8/2013 | Boese et al. |
| 9,125,676 | B2 | 9/2015 | Sahni |
| 9,222,996 | B2 | 12/2015 | Fujimoto et al. |
| 9,408,627 | B2 | 8/2016 | Sahni |
| 9,433,390 | B2 | 9/2016 | Nathaniel et al. |
| 10,123,767 | B2 * | 11/2018 | Andrews .............. A61B 8/0841 |
| 10,285,670 | B2 * | 5/2019 | Arimitsu ................ A61B 90/11 |
| 10,675,099 | B2 * | 6/2020 | Nakamura .......... A61B 17/3211 |
| 10,869,613 | B2 * | 12/2020 | Kato ...................... A61B 5/062 |
| 2004/0260312 | A1 | 12/2004 | Magnusson et al. |
| 2006/0229641 | A1 | 10/2006 | Gupta et al. |
| 2008/0208041 | A1 | 8/2008 | Gilboa |
| 2009/0112084 | A1 | 4/2009 | Piferi et al. |
| 2009/0171184 | A1 | 7/2009 | Jenkins et al. |
| 2009/0259122 | A1 | 10/2009 | Larson et al. |
| 2010/0063496 | A1 | 3/2010 | Trovato et al. |
| 2010/0082040 | A1 | 4/2010 | Sahni |
| 2011/0190787 | A1 | 8/2011 | Sahni |
| 2012/0022368 | A1 | 1/2012 | Brabrand et al. |
| 2013/0079678 | A1 | 3/2013 | Stein et al. |
| 2013/0079790 | A1 | 3/2013 | Stein et al. |
| 2013/0090554 | A1 | 4/2013 | Zvuloni et al. |
| 2013/0245461 | A1 | 9/2013 | Maier-Hein et al. |
| 2013/0345718 | A1 | 12/2013 | Crawford et al. |
| 2014/0022245 | A1 | 1/2014 | Brannan et al. |
| 2014/0128881 | A1 | 5/2014 | Tyc et al. |
| 2014/0276001 | A1 * | 9/2014 | Ungi ...................... A61B 5/064 |
| | | | 600/424 |
| 2016/0008074 | A1 | 1/2016 | Glossop |
| 2016/0038247 | A1 | 2/2016 | Bharadwaj et al. |
| 2016/0074063 | A1 * | 3/2016 | Arimitsu ............ A61B 10/0233 |
| | | | 606/130 |
| 2017/0014200 | A1 | 1/2017 | Onuma et al. |
| 2017/0020623 | A1 | 1/2017 | Glossop |
| 2017/0189127 | A1 | 7/2017 | Weir |
| 2017/0348061 | A1 | 12/2017 | Joshi et al. |
| 2018/0168682 | A1 | 6/2018 | Hazard, III et al. |
| 2018/0333208 | A1 | 11/2018 | Kotian et al. |

FOREIGN PATENT DOCUMENTS

| | | |
|---|---|---|
| JP | 2013-512748 A | 4/2013 |
| JP | 2014-534831 A | 12/2014 |
| JP | 2015-500664 A | 1/2015 |
| JP | 2015-047303 A | 3/2015 |
| WO | 2010/096149 A2 | 8/2010 |
| WO | 2014/201108 A1 | 12/2014 |

* cited by examiner

MEDICAL GUIDANCE SYSTEM AND METHOD USING LOCALIZED INSERTION PLANE

BACKGROUND OF THE INVENTION

Field of the Invention

The present disclosure relates to medical devices including medical guidance devices implementing an inertial measurement unit and a mechanical interface.

Description of the Related Art

In the medical field, accurate and precise positioning of medical instruments is critical. In the case of surgical procedures such as percutaneous intervention, exact placement of needle-like medical tools and instruments can mean the difference between success and failure of procedures. To aid in the positioning and to achieve an accurate and intuitive orientation of the medical tool, it has become common practice to track a medical tool such as a needle using different guiding type methods.

International application WO2010/096419 A2 discloses a needle-guiding device that provides tracking information of a needle-like medical tool by using tracking devices on the needle-like medical tools as well as on the patient. However, the device described does not provide information about cross-sectional images on an insertion plane when the physician makes a plan of insertion before bringing the needle to the patient. Therefore, the physician experiences difficulty planning the insertion, especially when the insertion is out of the axial imaging plane of the medical imaging device. Moreover, the device in WO2010/096419 A2 needs multiple tracking sensors in the system to accomplish the desired task. Thus, the system requires calibration for multiple tracking sensors adding an increased level of complexity in operation.

Additionally, U.S. Pat. No. 9,222,996 discloses a needle positioning system with an image guide system, a needle placement manipulator and a manipulator controller. The needle placement manipulator requires two rotatable ring structures with actuators, position sensors and fiducial markers, and directs a needle holder to a target position. Here, the image guide system acquires medical images, and can compute needle location and orientation in a medical image based on markers visible in the medical images, and can send the needle location and orientation to the manipulator controller. Then, the manipulator controller translates the needle location and orientation to command the actuators to direct the needle holder. The requirement for having two structures with actuators leads to a more complicated and bigger system to achieve proper medical device placement.

SUMMARY OF THE INVENTION

The various embodiments of the present medical guidance system and method, have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description of the Embodiments," one will understand how the features of the present embodiments provide the advantages described herein.

In a first embodiment, a medical guidance system includes an orientation localizer including at least one fiducial marker and having a localized plane, wherein the orientation localizes is mountable at a skin entry point on a patient, a computer configured to receive at least one medical image on the localized plane, register a position and orientation of the orientation localizer with the at least one medical image using the at least one fiducial marker, determine at least one cross sectional image based on the at least one medical image on the localized plane, and determine an insertion plane perpendicular to the localized plane, and an image display connected to the computer, wherein the image display displays the at least one cross sectional image on the localized plane and/or on the insertion plane.

In another embodiment, a medical guidance system includes an orientation localizer including at least one fiducial marker and having a localized plane, wherein the orientation localizer is mountable at a skin entry point on a patient, a computer configured to, receive at least one medical image on the localized plane, register a position and orientation of the orientation localizer with the at least one medical image using the at least one fiducial marker, wherein the position is registered by transforming local coordinates to satisfy the following equation:

$$T_G^{IM} = T_F^{IM}(p_i^{IM}) T_{MR}^{F}(\theta_E^{F}) T_G^{MR}(\theta_P^{MR})$$

wherein, $T_G^{IM}$ is a transformation to the coordinate for guidance of a medical tool based on the coordinate in the at least one medical image, wherein, $T_F^{IM}(p_i^{IM})$ is a transformation of the coordinate of the at least one fiducial marker from the coordinate of the medical images, wherein, $p_i^{IM}$ is a set of position vectors of all fiducial markers on the coordinate of the at least one medical image, wherein $T_{MR}^{F}(\theta_E^{F})$ is a transformation of the coordinate of a movable ring, wherein, $\theta_E^{F}$ is an angular position of a rotatable ring based on the coordinate of the at least one fiducial marker, wherein, $T_G^{MR}(\theta_P^{MR})$ is a transformation to a coordinate for guidance of the medical tool from the coordinate of the movable ring, wherein, $\theta_P^{MR}$ is an insertion angle on an insertion-plane indicator based on the coordinate of the movable ring, and determine at least one cross sectional image based on the at least one medical image on the localized plane, and determine an insertion plane perpendicular to the localized plane, and an image display connected to the computer, wherein the image display displays the at least one cross sectional image on the localized plane and/or on the insertion plane.

In yet another embodiment, a medical guidance system includes, a guidance device configured to guide a needle-like medical tool to an intended trajectory, and a computer configured to retrieve medical images and display the intended trajectory with the medical images, wherein the guidance device includes, a base plate including a base-plate opening, and a bottom surface configured to be mounted to a patient, a movable ring that attaches to the base plate, including a movable-ring opening aligned to the base-plate opening to form a main opening providing access to the patient, a guidance part mounting on the movable ring to guide the needle-like medical tool, and a rotary encoder including, a rotary scale mounted on the movable ring, a sensor head mounted on the base plate, a sensor circuit board connected to the sensor head, and configured to compute an angular position of the rotary scale by processing sensed signals from the sensor head, fiducial markers mounted on the base plate and configured to be visible in the medical images, and a circuit box including, a memory unit having device information to define geometrical relation between coordinates of the rotary encoder and of the fiducial markers, a microcontroller connected to the memory unit and the sensor circuit board, and configured to communicate with the computer, wherein the computer calculates geometry of the fiducial markers in the medical images with the coordinate of the medical images, and wherein the computer or the microcontroller computes a coordinate of the guidance device with the coordinate of the medical images by using the device information in the memory unit and the geometry of the fiducial markers calculated by the computer.

DETAILED DESCRIPTION OF THE EMBODIMENTS

Example devices, methods and systems are described herein. Any example embodiment or feature described herein is not necessarily to be construed as preferred or advantageous over other embodiments or features. The example embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the figures should not be viewed as limiting. It should be understood that other embodiments might include more or less of each element shown in a given figure. Further, some of the illustrated elements may be combined or omitted. Yet further, an example embodiment may include elements that are not illustrated in the figures.

Exemplary embodiments of the present disclosure provide for accurately guiding and inserting a medical needle into a medical patient. Pursuant to these exemplary embodiments, a medical practitioner can utilize cross-sectional images on an insertion plane of the medical patient before delivery of the medical needle to the medical patient.

Figure 1:
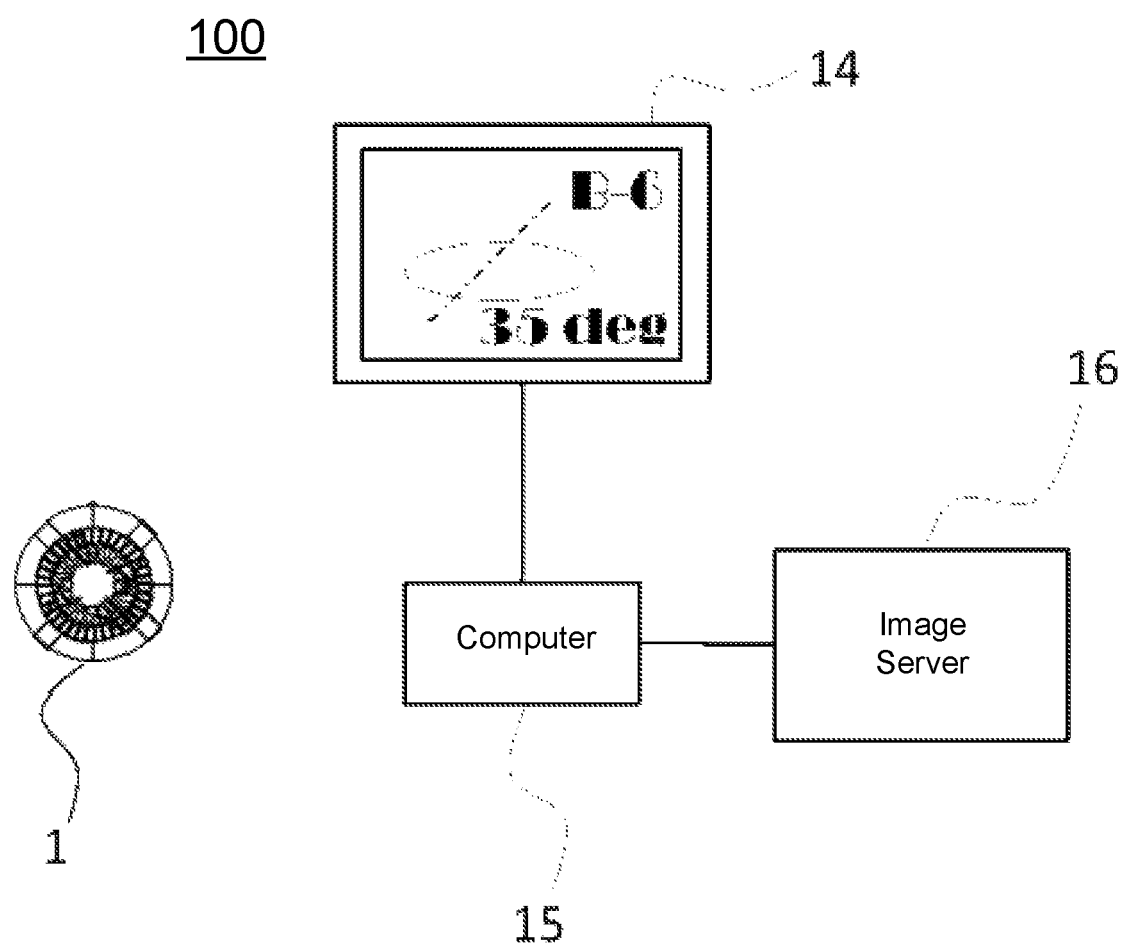
FIG. 1 is a functional block diagram illustrating a medical guidance system according to an exemplary embodiment of the present disclosure.
Figure 2A:
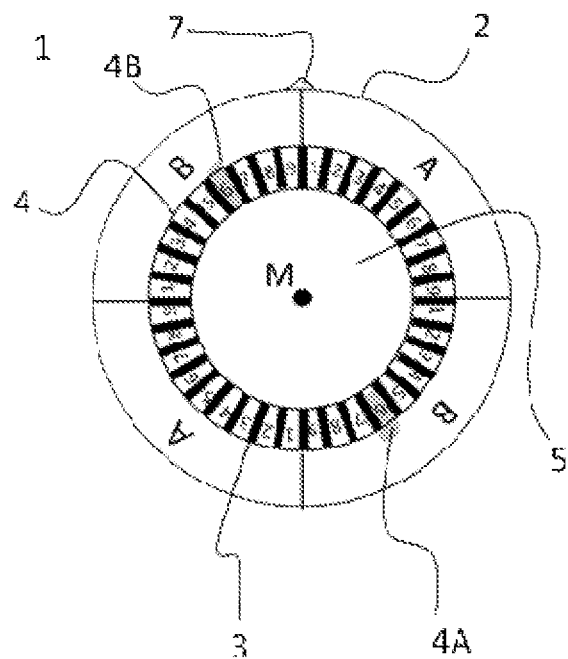
FIG. 2A is a top view of an orientation localizer in a medical guidance device according to a first embodiment of the present disclosure.
Figure 2B:
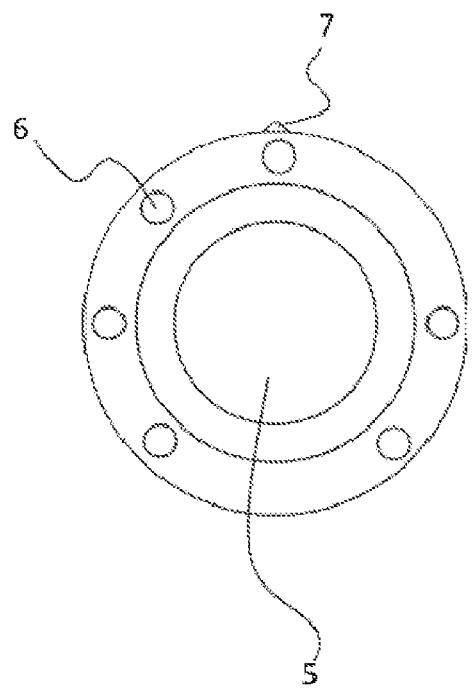
FIG. 2B is a bottom view of an orientation localizer in a medical guidance device according to a first embodiment of the present disclosure.

FIG. 1 depicts a system of a medical device guidance system 100 according to an exemplary embodiment of the present disclosure. The medical guidance device system 100 includes an orientation localizer 1, computer 15, image server 16 and image display 14. The computer 15 and the image display 14 are communicatively-coupled via a bus to transmit/receive data between each other. Moreover, the computer 15 is connected and communicates with an image server 16 that is external of the medical guidance device system 100. The image server 16 includes but is not limited to a DICOM™ server connected to a medical imaging device including but not limited to a CT and/or MRI scanner. The computer 15 processes data provided by the orientation localizer 1 and data provided by images stored on the image server 16 in order to display images onto the image display 14. FIGS. 2A & 2B describe and show the orientation localizer 1, which can be but is not limited to a ring-shaped sticker, in detail.

FIGS. 2A and 2B show a top view and bottom view, respectively, of the orientation localizer 1 included in the medical device guidance system 100 according to an embodiment of the present disclosure. The orientation localizer 1 is a ring-shaped device able to adhere to a patient's skin and includes a major angular scale 2, a minor angular scale 3, templates 4 (including templates 4A and 4B), opening 5, fiducial markers 6 and reference marker 7. The major angular scale 2 and the minor angular scale 3 are arrayed around center M. Template 4A and template 4B are printed with numbers (1-9) between adjacent angular minor scale 3. Major angular scale 2 and minor angular scale 3 are reflections of each other and symmetrical as are template 4A and template 4B. On the backside of angular major scale 2, fiducial markers 6 are arrayed in a circular layout around center M. The fiducial markers 6 are asymmetric in their rotation around center M.

Figure 3:
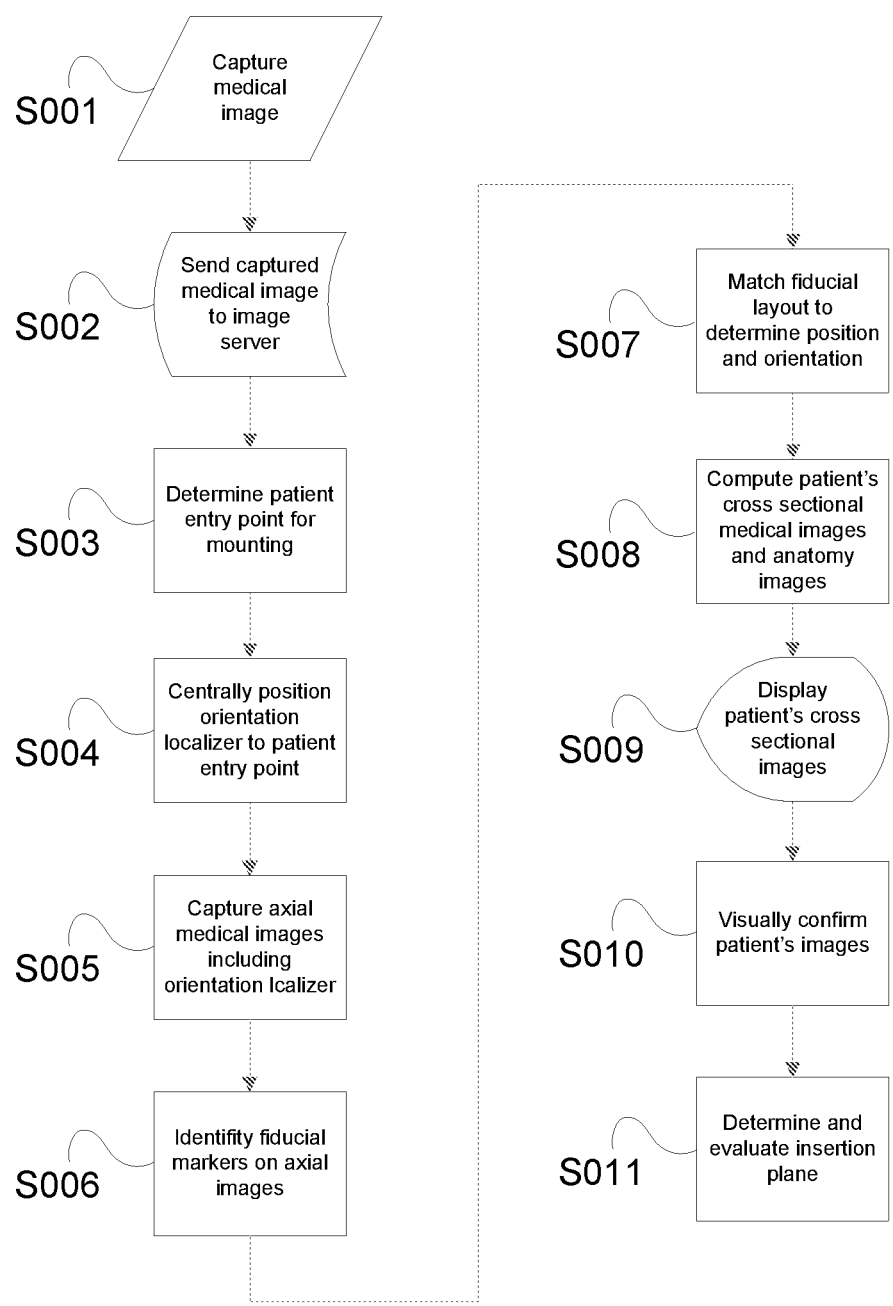
FIG. 3 is a flowchart illustrating a process relating to guidance of a needle using the medical guidance system according to a first embodiment of the present disclosure.

FIG. 3 is a flowchart illustrating a process for guidance of a needle according to an exemplary embodiment of the present disclosure. Initially, in Step S001 a medical image is captured, for example a CT scan image, using a medical imaging device.

Then, in Step S002 the medical image is sent to the image server 16, which is communicatively-coupled to the medical imaging device, where the medical image is stored.

Using the medical image stored in the medical imaging server 16, in Step S003 a physician determines the entry point on a patient where a needle will be inserted. This entry point is where the orientation localizer 1 will be mounted to the skin of the patient.

Upon mounting, in Step S004 the orientation localizer is positioned so that center M of the orientation localizer is at a position O marking the entry point on the patient.

Figure 6A:
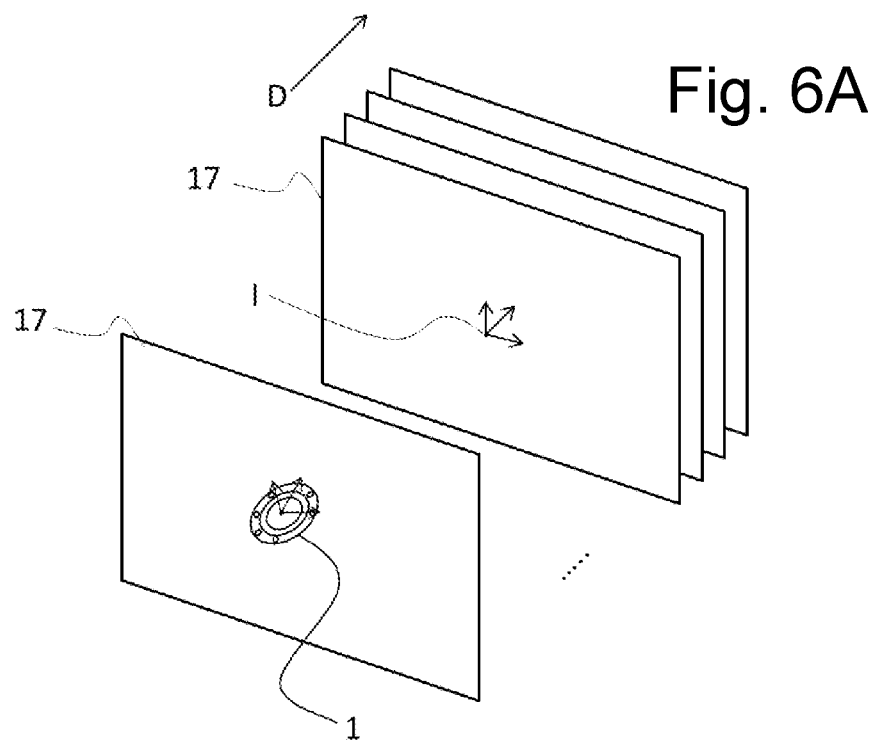
FIGS. 6A & 6B show captured axial medical images according to an exemplary embodiment of the present disclosure.

Next, in step S005 the physician performs image registration using the medical imaging device to obtain a set of medical images. In the image registration process, the medical imaging device captures axial medical images 17 along axial direction D, as shown in FIG. 6A, which is in the longitudinal direction of the patient's bed. With orientation localizer 1 mounted on the patient and during the capturing of the medical image set, orientation localizer 1 appears in the captured multiple axial medical images 17 as seen in FIG. 6A. FIG. 6A also shows the medical image set including the orientation localizer 1.

In Step S006 the fiducial markers 6 are automatically identified by the computer 15 by using an appropriate image processing algorithm to detect the circular shape of the orientation localizer 1, including but not limited to the Hough transformation.

Next, in Step S007 the computer 15 identifies the position and the orientation of the orientation localizer 1 by matching a known fiducial layout with the fiducial layout that the computer 15 identifies from the axial medical images 17. In this embodiment, since the fiducial markers 6 are asymmetric along a circumference of the circular array of the fiducial markers 6, the computer 15 can determine the orientation along the circumference of the fiducial layout while the center of the circumference of the identified fiducial layout is identified as center M.

Figure 6B:
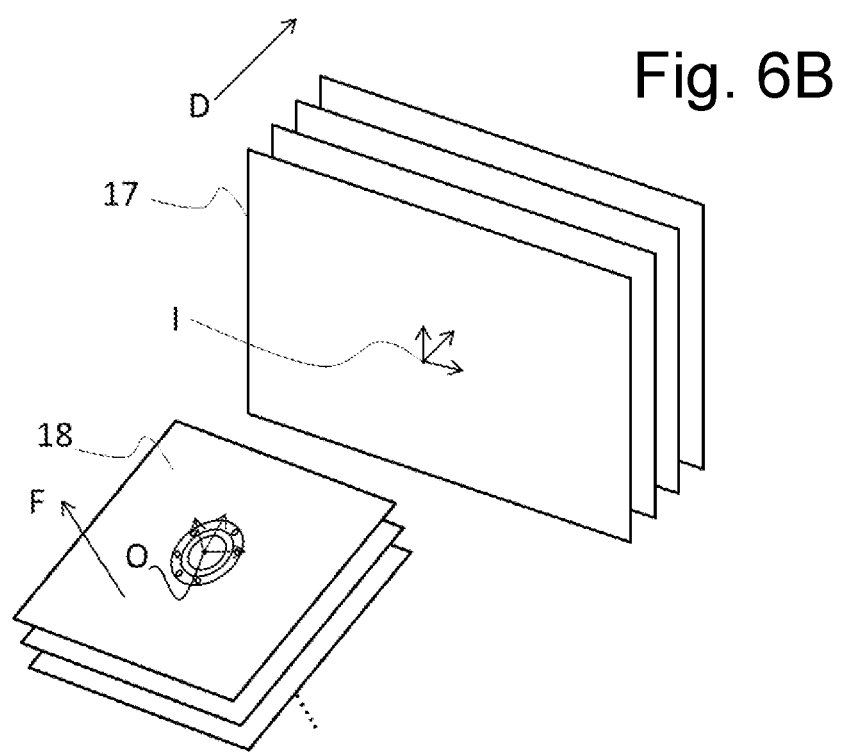
Figure 8:
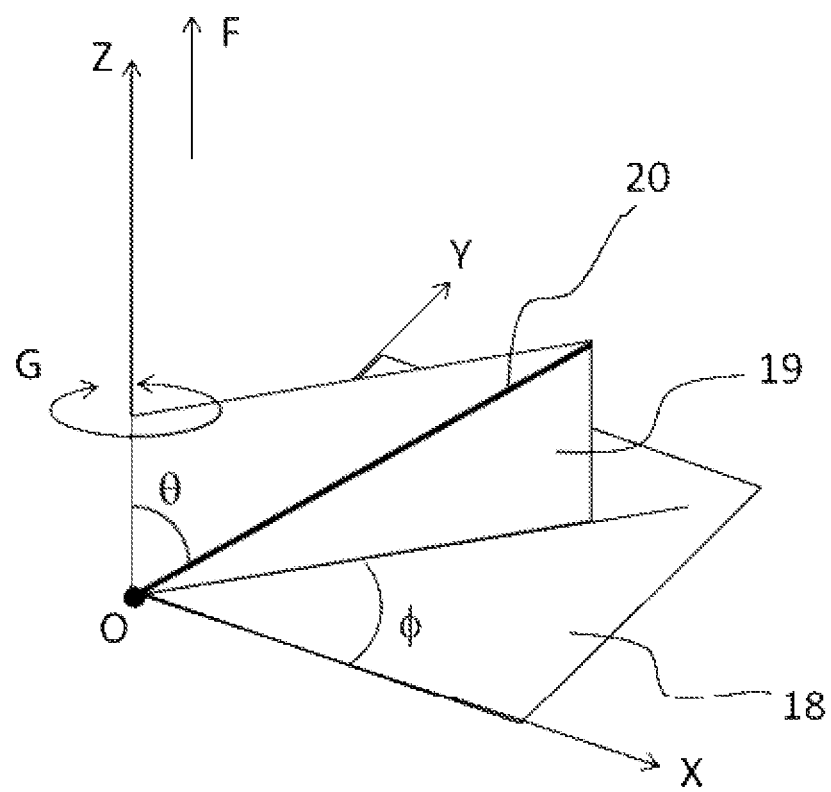
FIG. 8 is a perspective view showing an insertion plane and localized plane according to an exemplary embodiment of the present disclosure.

In Step S008, after the computer 15 determines the position and the orientation of the orientation localizer 1, the computer 15 automatically determines cross sectional medical images of the patient's anatomy on localized plane 18 as shown in FIG. 6B. The localized plane 18 has a Z-axis where the local coordinate O of the orientation localizer 1 is a normal vector F of the localized plane 18. The cross sectional medical images on the localized plane 18 can be defined on any plane parallel to the X-Y plane of the local coordinate O. For example, in FIG. 6b the localized plane 18 is shown. The computer 15 then concurrently determines medical images of the patient's anatomy on insertion plane 19 as shown in FIG. 8. The insertion plane 19 is perpendicular to the localized plane 18 and includes an origin of the local coordinate O of the orientation localizer 1. The insertion plane 19 can be defined along rotational direction G around the Z-axis of the local coordinate O of the orientation localizer 1. For example, an angular position of the insertion plane 19 is defined as angle $\phi$, which is an angle between the insertion plane 19 and the X-axis of the local coordinate O.

In Step S009 the computer 15 displays the cross sectional images of the patient's anatomy on the localized plane 18 and/or on the insertion plane 19 on the image display 14. The computer 15 can also display the angular portion of the templates 4 corresponding to the angular position of insertion plane 19, i.e. the angle $\phi$. In FIG. 2, the image display 14 shows B-6 as the angular position of the templates 4.

In Step S010, the physician can visually confirm the cross sectional images on the localized plane 18 or on the insertion plane 19 and can make an insertion plan by defining a target position of the tip of the medical tool.

Upon confirmation, in Step S011 the physician can determine an appropriate insertion plane 19 and mark the templates 4 with the selected insertion plane 19, for example templates 4A and 4B are shown in FIG. 2A. Also, the physician can confirm orientation of the line connected template 4A and 4B in relation to the reference marker 7. The reference marker 7 directs to the X-axis of the local coordinate O. Therefore, the physician can easily find the template 4A by using both the template position (B-6 in FIG. 1) and angle $\phi$ (35 deg in FIG. 1).

After marking on the templates 4A & 4B, the physician can use the marked templates 4A & 4B as landmarks of the insertion plane 19 where the physician plans to insert a medical tool. Since the orientation localizer 1 is mounted on the patient, the orientation localizer 1 can provide an insertion landmark even when the patient moves accidentally.

During the procedure, the medical guidance device can update the image registration of the orientation localizer 1 in every image acquisition by performing automatic image registration.

Figure 4:
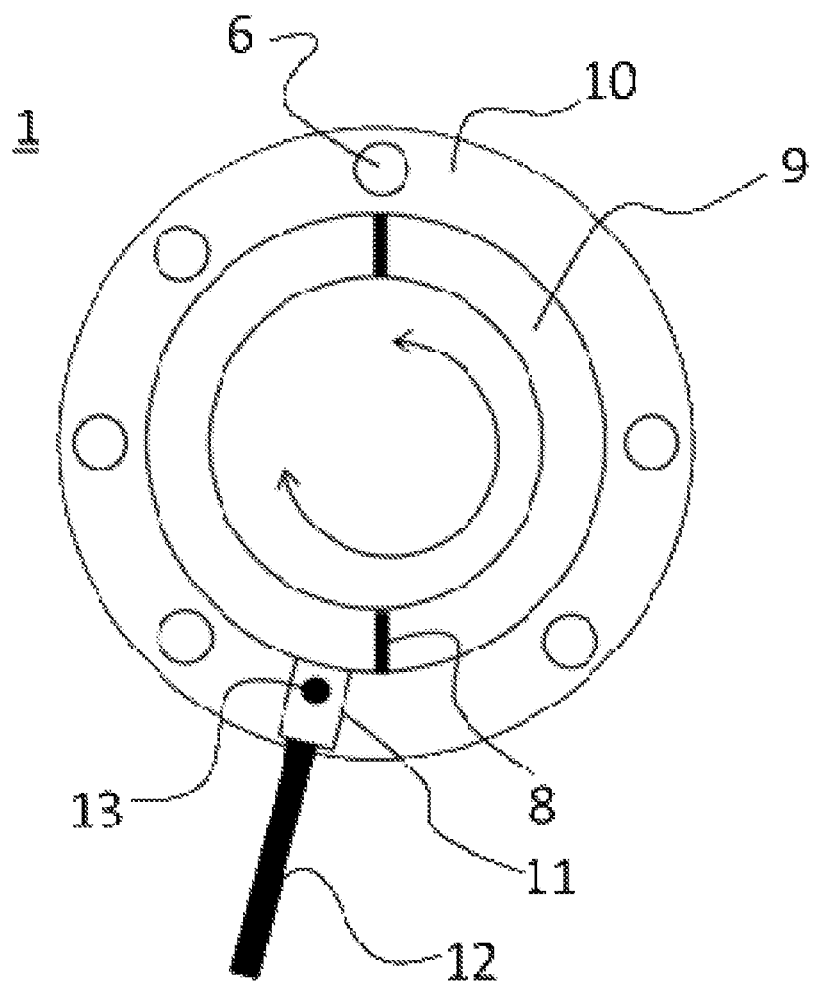
FIG. 4 is a plan view of an orientation localizer according to a second embodiment of the present disclosure.

FIG. 4 is a plan view of an orientation localizer 1 according to another embodiment of the present disclosure. Here, orientation localizer 1 includes a rotatable body 9 and a stable body 10. The rotatable body 9 is a ring that can rotate against the stable body 10 and has an insertion-plane indicator 8. The stable body to includes the fiducial markers 6, socket n and communication cable 12. Moreover, the socket 11 has a zero position marker 13.

In the orientation localizer 1, the rotary encoder is located in the stable body 10. Also, the rotary encoder scales are located in the rotatable body 9. The rotary encoder measures the rotation angle from the zero position marker 13. The communication cable 12 powers the rotary encoder and allows two-way communication to send and receive the rotary encoder signals to/from the computer 15.

Figure 5:
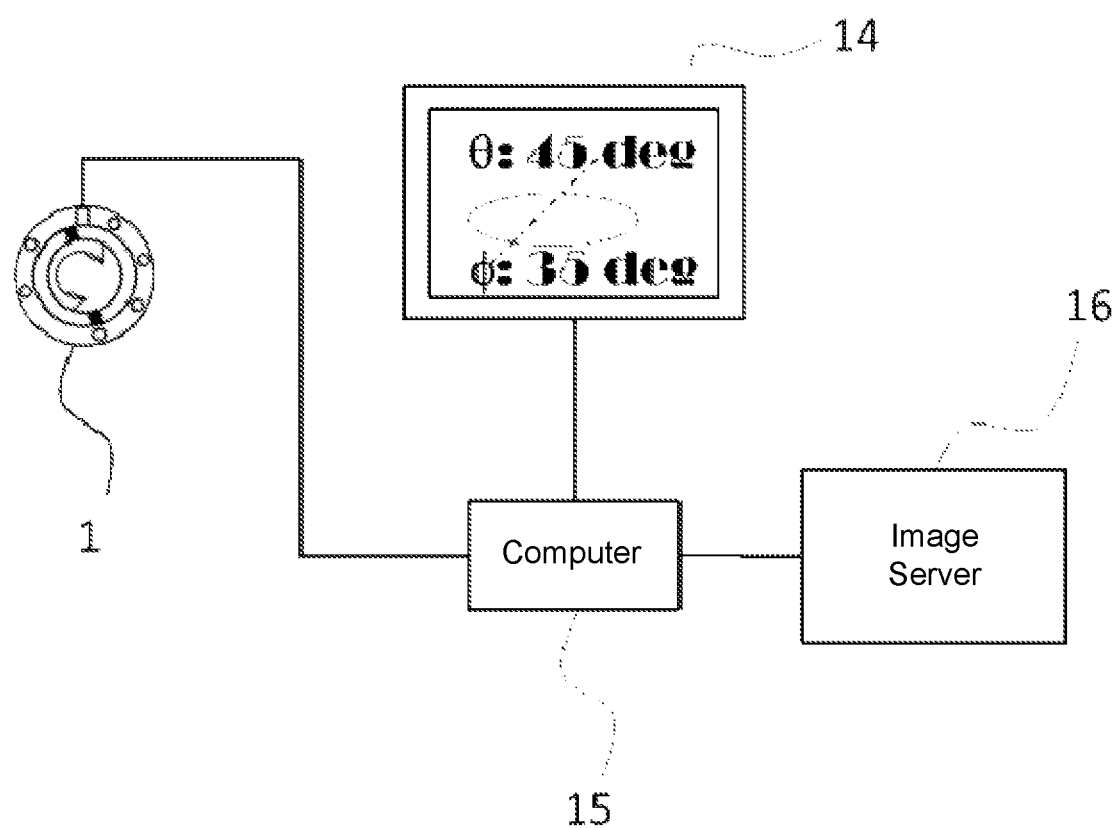
FIG. 5 depicts a system of a medical device guidance system according to a second exemplary embodiment of the present disclosure.

FIG. 5 depicts a system of a medical device guidance system according to yet another embodiment of the present disclosure and will be described with reference to FIGS. 4 and 8. The computer 15 determines the cross-sectional images on the insertion plane 19 corresponding to the rotation of the rotatable body 9 by using the rotary encoder signals via the communication cable 12. The computer 15 also updates the cross-sectional images in real time while synchronizing to the rotatable body 9. This allows a physician to confirm different images by rotating the rotatable body 9 without having to refer back and forth between the image display 14 and the patient. Once the physician finds an optimal insertion plane 19, the physician can use the insertion-plane indicator 8 as a landmark for the optimal insertion plane 19.

Upon determining the optimal insertion plane 19, the physician then determines the target position of the tip of the medical tool on the insertion plane 19. Since the skin entry point is already determined, a needle trajectory 20 is defined by connecting the skin entry point and the target position of the tip of the medical tool. Afterwards, the computer 15 determines an insertion angle $\theta$ between a needle trajectory 20 and the Z-axis of the local coordinate O. This allows the computer 15 to display the insertion angle $\theta$ as well as the angle $\phi$ of the insertion plane on the display 14.

The physician can then use these angles to guide the medical tool to the planed needle trajectory 20 by using the orientation localizer 1 on the patient as a landmark for both the insertion angle $\theta$ as well as the angle $\phi$ of the insertion plane 19. As an option, the insertion angle $\theta$ can be replaced by different notation of the insertion angle $\theta$. For example, the computer 15 can provide calculations based on the height of the medical tool on the circumference of the rotatable body 9 to the physician.

Figure 7:
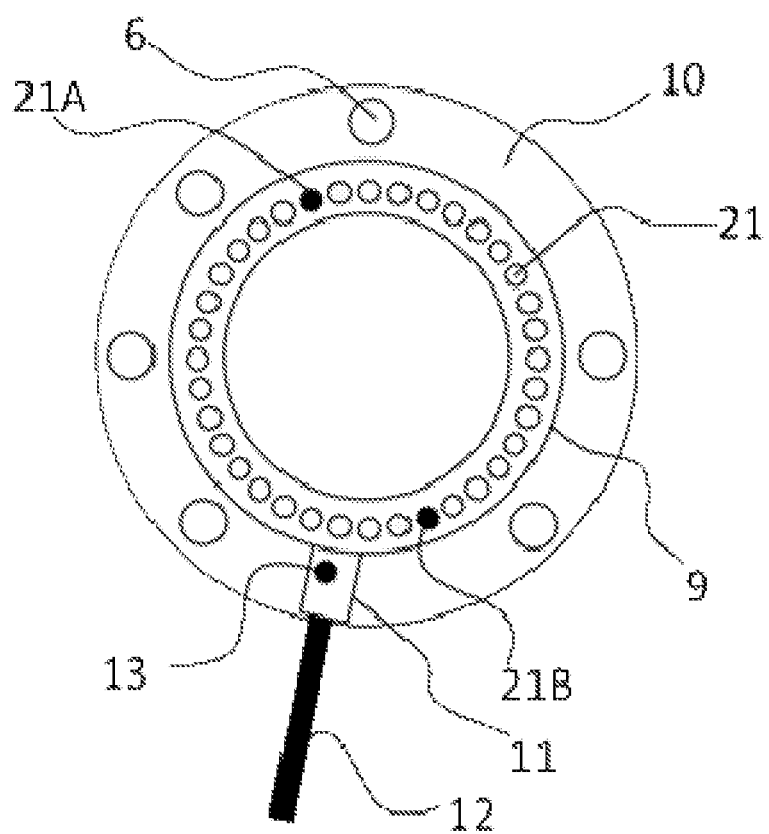
FIG. 7 is a plan view of an orientation localizer of yet another embodiment of the present disclosure.

FIG. 7 is a plan view of an orientation localizer 1 of yet another embodiment of the present disclosure. Here, the orientation localizer 1 is integrated within the rotatable body 9 and the orientation localizer 1 has a touch screen 21 with LEDs arrayed along the circumference of the rotatable body 9. The touch screen 21 with LEDs can detect the touch of a user and change the position of the lit LEDs 21A & 21B to indicate the insertion plane 19.

Since the rotatable body 9 does not include a physically rotatable part, the orientation localizer 1 is able to be packaged with a sterile cover without pinching the packaging between the rotating and stable parts thus reducing the presence of a narrow gap between parts. Accordingly, the orientation localizer 1 can reduce difficulty in sterilization and make management of sterilization easier.

Figure 9:
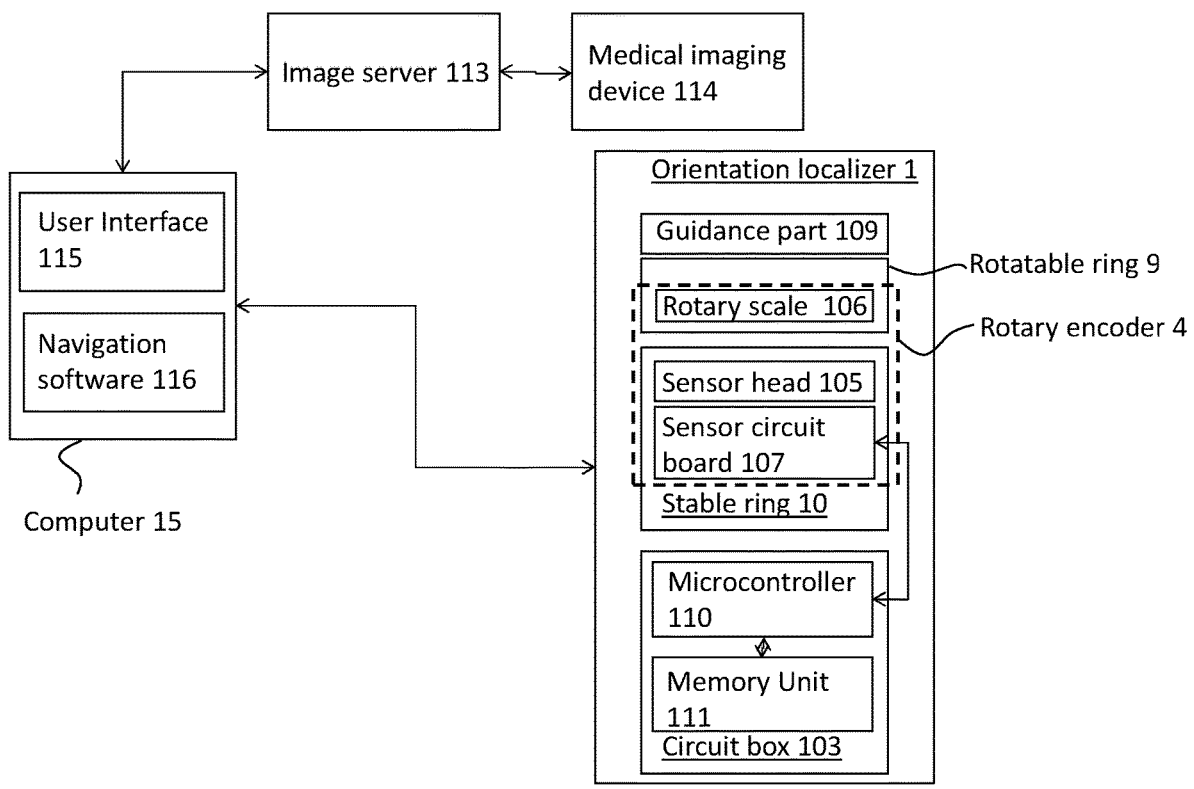
FIG. 9 is a functional block diagram illustrating a medical guidance system according to another embodiment of the present disclosure.

FIG. 9 is a functional block diagram illustrating a medical guidance system 100 according to another embodiment of the present disclosure. In this embodiment, the medical guidance system 100 transmits and receives data to/from an image server 113 that receives image information from a medical imaging device 114. The medical guidance system 100 includes a computer 15 and an orientation localizer 1 that are communicatively-coupled via a bus. The image server 113 includes, but is not limited to, a DICOM™ server or equivalent that receives and stores image information from the medical imaging device 114. The medical imaging device 114 includes, but is not limited to, a computed tomography (CT) scanner, magnetic resonance imaging (MRI) scanner, positron emission tomography (PET) scanner, single-photon emission computed tomography (SPECT) scanner and/or fluoroscopy scanner.

The computer 15 of the medical guidance system 100 includes a user interface 115 allowing a user to access and control the computer 15 and navigation software 116 to determine proper insertion angles of a needle-like medical device into a medical patient based on image data received from the medical imaging device 114 and stored in the image server 113. Additionally, the navigation software 116 provides a medical professional information including, but not limited to, protocols involving the use of the orientation localizer 1 and visual orientation and location information of the orientation localizer 1.

The orientation localizer 1 includes a guidance part 109, a rotatable ring 9, a stable ring 10, and a circuit box 103. The rotatable ring 9 includes a rotary scale 106. The stable ring 10 has a sensor head 105 and a sensor circuit board 107. The circuit box 103 includes a microcontroller 110 and a memory unit 111. Portions of the rotatable ring 9 and the stable ring 10 make up a rotary encoder 4. The rotary encoder 4 includes the rotary scale 106 of the rotatable ring 9 and the sensor head 105 and sensor circuit board 107 of the stable ring 10.

In yet another embodiment of the present disclosure, the medical guidance system 100 operates very similarly with the orientation localizer 1 instead being replaced by a guidance device. The guidance device includes the elements of the orientation localizer 1 with the small difference of the stable ring 10 being replaced by a base plate and the rotatable ring 9 being replaced by a moveable ring. All other elements of the system remain the same as those shown in FIG. 9.

Figure 10A:
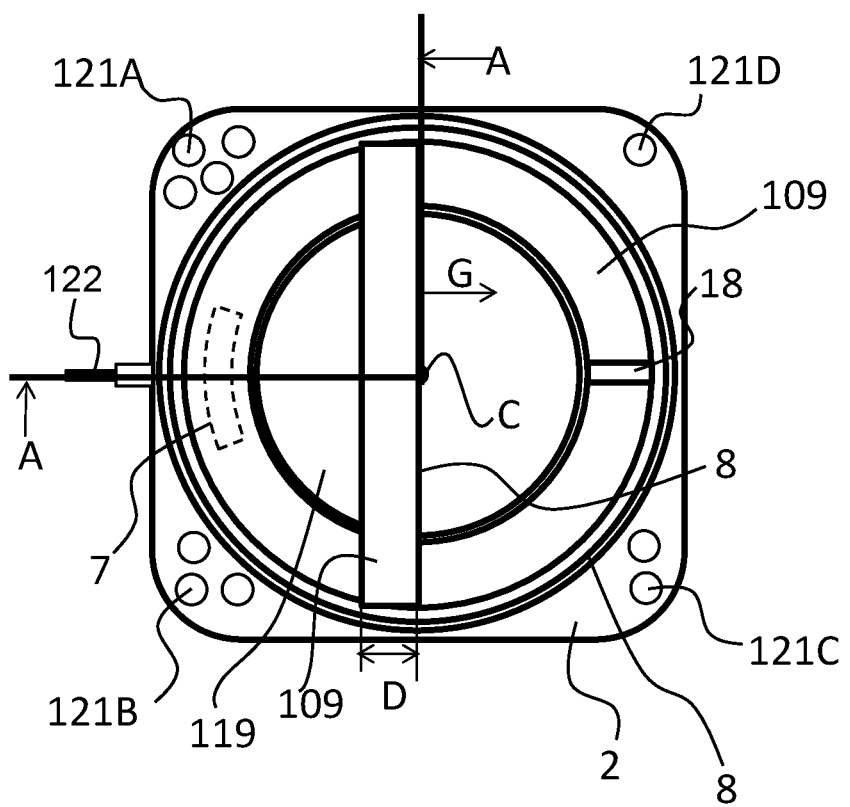
FIGS. 10A and 10B are plan views of the orientation localizer according to the embodiment as described in FIG. 9 of the present disclosure.
Figure 10B:
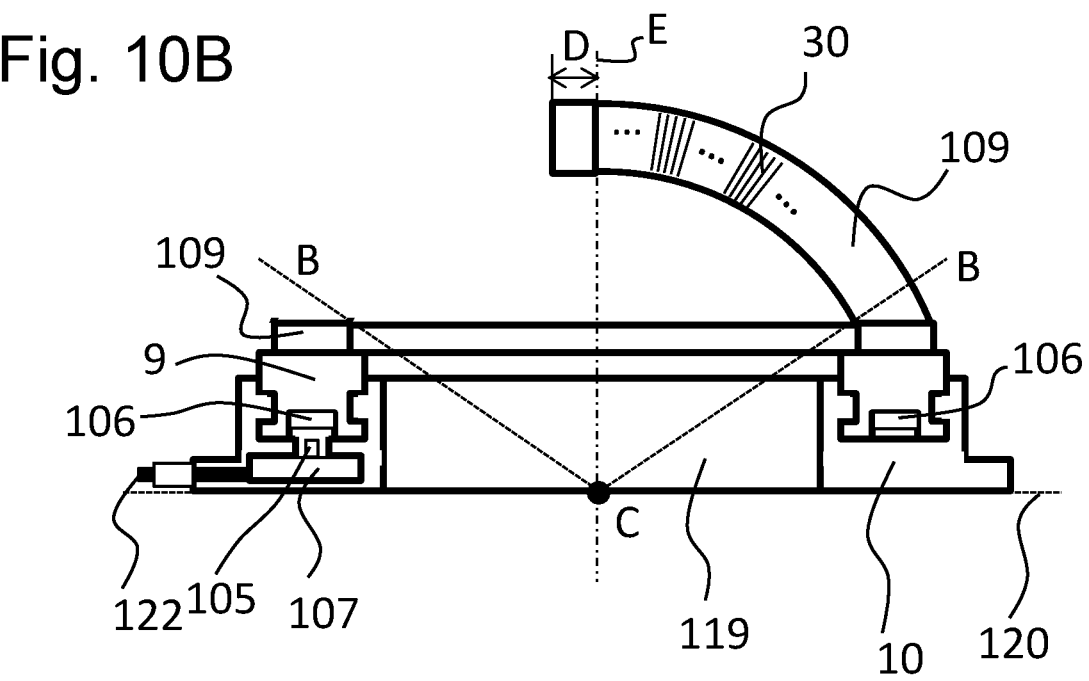

FIGS. 10A and 10B are plan views of the orientation localizer 1 according to the embodiment as described in FIG. 9 of the present disclosure. FIG. 10A is a top view of the orientation localizer 1 and FIG. 10B is a cross sectional view at an A-A line as shown in FIG. 10A. The A-A line bends at point C at a right angle to see two cross sectional views in the one figure shown in FIG. 10B. In yet another embodiment of the present disclosure, all features disclosed in FIGS. 10A and 10B are similar with the orientation localizer 1, stable ring 10 and rotatable ring 8 being replaced by a guidance device, a base plate and a moveable ring, respectively.

In FIG. 10B the stable ring 10 has a mounting surface 120 situated on the bottom. The mounting surface 120 is mounted on the skin surface of a patient and the stable ring 10 adheres to the skin of the patient via the mounting surface 120.

In FIG. 10A, the stable ring 10 includes fiducial markers 121A, 121B, 121C and 121D at four corners. The fiducial markers 121A, 121B, 121C and 121D are visible optically as well as in CT and X-ray images utilizing radio-opaque material. The radio-opaque material can be, but are not limited to, plastic including fillers of Barium Sulfate, bismuth subcarbonate, bismuth oxychloride, tungsten.

At each corner, the fiducial markers form a cluster of markers with different numbers of fiducial markers than each other. Therefore, the position and the orientation of the stable ring 10 can be geometrically distinguished using only the fiducial markers 121A, 121B, 121C and 121D in the CT and X-ray images.

Moreover, as shown in FIG. 9, the stable ring 10 includes portions of the rotary encoder 4, which includes sensor head 105 and the sensor circuit board 107. The sensor head 105 faces the rotary scale 106, which is mounted on the rotatable ring 9, and is electrically connected to the sensor circuit board 107. The sensor circuit board 107 processes measurement signals of the angular position of the rotary scale 106 by the sensor head 105, and outputs the angular position to the microcontroller 110.

The stable ring 10 is ring-shaped and engages with the rotatable ring 9. Referring to FIG. 10B, the rotatable ring 9 is rotatable around the axis E with a rail on the stable ring 10. The axis E passes through point C on the mounting surface 120. Also, stable ring 10 and rotatable ring 9 have seal structures to protect sensor head 105 and rotary scale 106 from contamination in an external environment.

The rotatable ring 9 has the rotary scale 106 where the rotary scale 106 is fixed on rotatable ring 9 and can rotate with rotatable ring 9. The sensor head 105, rotary scale 106 and sensor circuit board 107 form the rotary encoder 4. Rotary encoder 4 measures an angular position of the rotatable ring 9 against the stable ring 10.

The rotatable ring 9 mechanically connects to guide part 109. The guide part 109 is detachable from rotatable ring 9 with a mechanical coupling between the rotatable ring 9 and the guide part 109. As shown in FIGS. 10A and 10B, guide part 109 includes a ring frame and an arc shape guide. The ring frame is monolithically made with the arc shape guide and includes space 18 to release a needle-like medical tool (not shown). The arc shape guide bridges on the ring frame over the main opening 119. The arc shape guide also includes the insertion-plane indicator 8 and angular reference marks 30. The insertion-plane indicator 8 includes axis E and has thickness D to create a guidance area toward arrow G as shown in FIG. 8.

The angular reference marks 30 are line marks to signify an angle around point C on the insertion-plane indicator 8. By rotating the rotatable ring 9 around axis E, the angular reference marks 30 also rotate around axis E with the insertion-plane indicator 8. By using the angular reference marks 30 and the rotatable ring 9, the orientation localizer 1 localizes the insertion plane and further localizes fine grids of a remote center of motion with point C. The grids are cone-shaped grids with generator B along the point C as a pivot.

The remote center of motion models a physician's maneuver of a needle-like medical tool. Thus, point C is aligned to a skin entry point of the medical tool, which is defined by considering obstacles close to the patient's skin. With the fixed point C, the physician can select an intended trajectory to the target by using an appropriate position of the rotatable ring 9 and the angular reference marks 30.

After determining the position of rotatable ring 9 and the angular reference marks 30, the physician can insert the needle-like medical tool with guidance from the insertion-plane indicator 8 at the target angular reference marks 30.

Figure 11A:
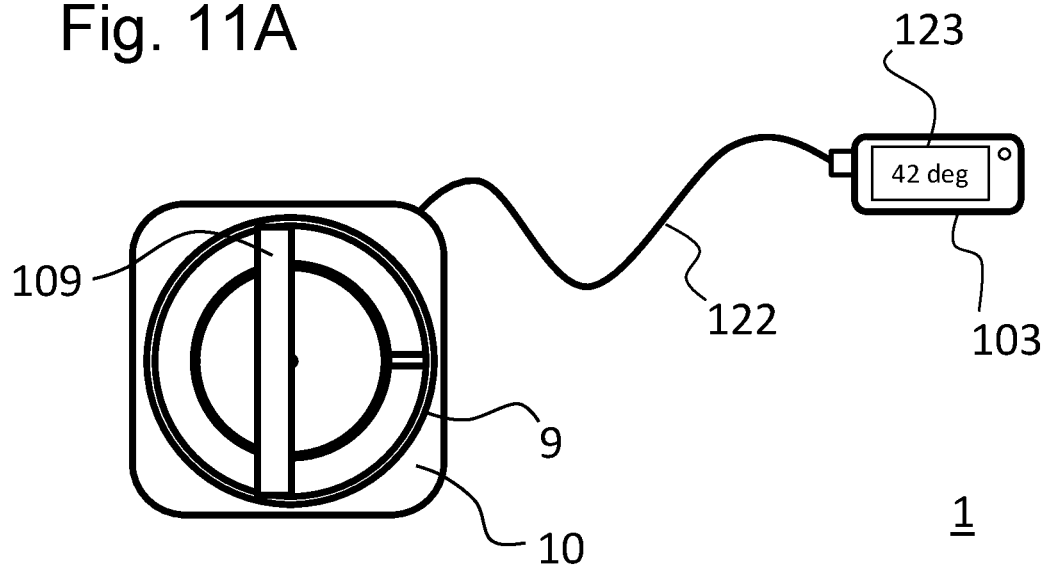
FIGS. 11A and 11B are schematic illustrations of the orientation localizer focusing on a circuit box according to additional embodiments of the present disclosure.

FIG. 11A is a schematic illustration of the orientation localizer 1 according to yet another embodiment of the present disclosure, more specifically, the configuration of the circuit box 103 with the rest of the medical device guidance system 100. In FIG. 11A the circuit box 103 as described in FIG. 9, includes a microcontroller 110, a memory unit 111, a battery (not shown), and a wireless communication unit (not shown).

The microcontroller 110 processes information from the computer 15 and the sensor circuit board 107 and the microcontroller 110 communicates with the computer 15 and the sensor circuit board 107 to exchange commands and target information between them. Specifically, the microcontroller no initiates and sends the angular position of the rotatable ring 9 measured by the rotary encoder 4 to the computer 15, as needed.

The microcontroller 110 is also electrically-connected to the memory unit 111. The memory unit in stores at least transformation matrices of the orientation localizer 1 based on a local coordinate of the orientation localizer 1, which is determined as design. The microcontroller 110 then retrieves and sends these transformation matrices in the memory unit in to the computer 115, when the navigation software 116 requires them.

Specifically, the circuit box 103 in FIG. 11A is electrically-connected to the rotary encoder 104 at the sensor circuit board 107 in the stable ring 10 via the electric cable 122, as a separate part from the stable ring 10. Consequently, the circuit box 103 in FIG. 11A can be placed bedside or near the patient close to an area of the intervention, but separated place from the stable ring 10. With the circuit box 103 in FIG. 11A, the stable ring 10 can reduce the footprint and reduce the area needed for the intervention. Also, the circuit box 103 in FIG. 11A includes an indicator 123. The indicator 123 reflects the real-time angular position of the rotatable ring 9 with a digital indicator. Moreover, the indicator 123 displays different information about the orientation localizer 1, for instance the target angular position of the rotatable ring 9, the target angular reference mark, comparison between the target and current angular position of the rotatable ring 9, and the remaining battery power. With the indicator 123 on the circuit box 103 in FIG. 9A, the physician can confirm the information on the orientation localizer 1 on the spot without having to leave the patient and the area of the intervention.

Figure 11B:
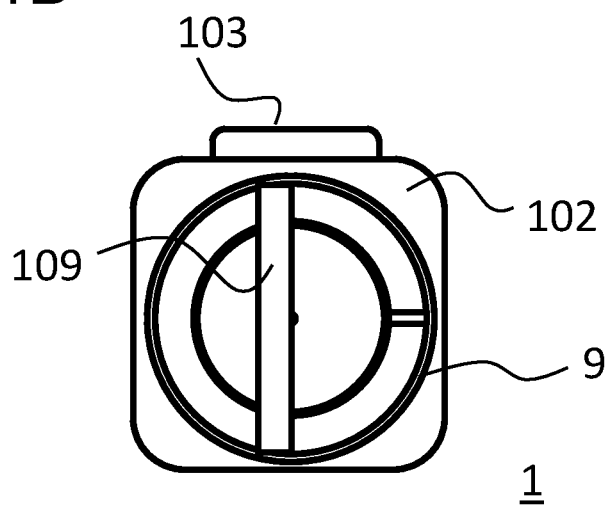

FIG. 11B shows a schematic illustration of the orientation localizer 1 according to another embodiment of the present disclosure, more specifically, the configuration of the circuit box 103 with the rest of the components. In FIG. 11B the circuit box 103 includes a microcontroller 110, a memory unit 111, a battery (not shown), and a wireless communication unit (not shown). This is similar to the embodiment described in FIG. 11A, however the circuit box 103 in FIG. 11B is monolithically fixed on the stable ring 10. Therefore, the risk of tangling cables with other objects in the surgical field are greatly reduced.

Figure 12:
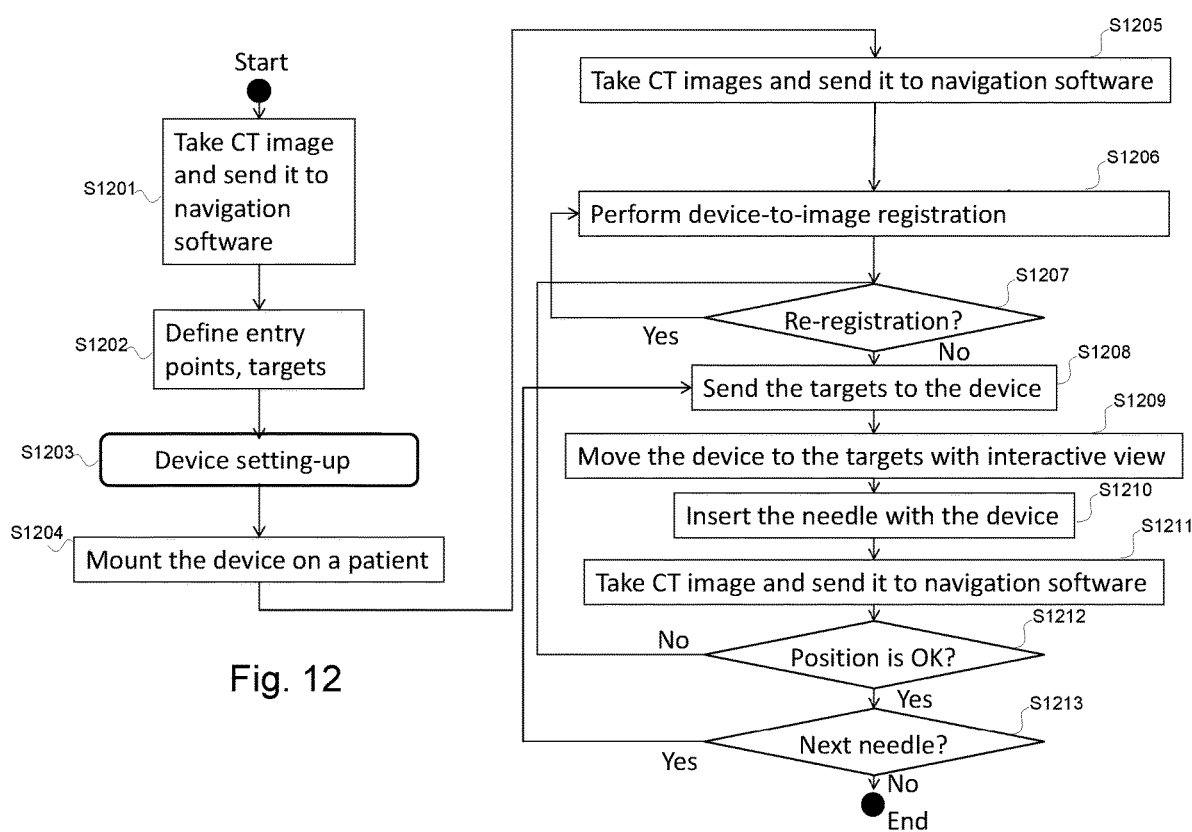
FIG. 12 is a flowchart illustrating a process for guidance of a needle using a medical guidance system according to an exemplary embodiment of the present disclosure.

FIG. 12 is a flowchart illustrating a process for guidance of a needle using the medical guidance system 100 of the present disclosure. In step S1201 a physician takes medical images using a medical imaging device 114. The medical device 114 is a CT scanner in this particular embodiment, and sends the CT images to the navigation software 116 in the computer 15 via the image server 113.

At step S1202, with the CT images, the physician defines targets for percutaneous intervention with a needle-like medical tool and the skin entry point. At the same time, by connecting the target to the skin entry point, the physician can determine the plane for the trajectory of insertion of the needle-like medical tool using the navigation software 116. Also, in this step, the physician marks the skin entry point on the patient which is standard practice using for example, grid visible markers on the patient.

In step S1203 the physician sets up the device to calibrate it and sets a proper initial state of the orientation localizer 1. More specifically, setting up the rotary, encoder 104 to establish an original zero position properly; this will be explained in more detail in FIG. 14.

After the setting up the device, in Step S1204 the physician mounts the orientation localizer 1 onto the patient aligning the point C in FIGS. 10A & 10B to the skin entry point and affixes the orientation localizer 1 with adhesive tape.

In Step S1205, after the device mounting, the physician takes CT images including the orientation localizer 1 and sends the CT images to the navigation software 116. Using the CT images with the orientation localizer 1 showing, in Step S1206 the physician conducts device-to-image registration. In this step, the navigation software 116 recognizes the position and orientation of the orientation localizer 1 on the patient in the CT images, i.e. in the coordinate of the CT image, by using fiducial markers 121A, 121B, 121C and 121D as described in FIGS. 10A and 10B. This fiducial marker detection can be manually performed by physician instruction with user interface 115 or, can be fully automated by using a computer algorithm. The navigation software 116 can also reflect the plan of the trajectory with two device parameters, which are angular position of the rotatable ring 9 ($\theta_E^F$) and insertion angle on the insertion-plane indicator 8 ($\theta_E^F$) at this step. Device-to-image registration will be discussed further with respect to FIG. 13.

In step S1207, the physician can be asked whether the device-to-image registration is appropriate or not by the navigation software 116. If not (no is Step S1207), the physician can conduct Step S1206 the device-to-image registration again.

If the device-to-image registration is appropriate (Yes in Step S1207), flow proceeds to Step S1208 where the physician can send the target device parameters $\theta_E^F, \theta_F^{MR}$ to the microcontroller 110.

Afterwards in Step S1209, the physician manually rotates the rotatable ring 9 while the navigation software interactively updates the cross sectional image on the guide surface by using the real-time angular position of the rotatable ring 9 from the microcontroller 110. Also, the microcontroller no compares the real-time angular position of the rotatable ring 9 with the target angular position. Once the rotatable ring 9 reaches the target angular position, the microcontroller informs the navigation software 116 and indicator 123 of the end of targeting of the rotatable ring 9. Then, the navigation software 116 and/or indicator 123 informs the physician of the end of targeting.

Upon establishing the target angular position of the rotatable ring 9, in Step S1210 the physician picks the specific angular reference mark 30 indicated by the target insertion angle on the insertion-plane indicator 8 and with the specific angular reference mark 30, the physician inserts the needle-like medical tool from the skin entry point to the target.

In Step 1211 after the first attempt of the insertion, the physician takes CT images of the inserted needle-like medical tool, the orientation localizer 1, and the CT images and sends them to the navigation software 116. With the CT images of the inserted needle-like medical tool, the physician evaluates the position of the inserted needle-like medical tool.

In step S1212, the position of the inserted needle-like medical tool is checked and if the physician thinks the position is suboptimal (No in Step S1212), flow proceeds back to Step S1208 where the physician can update the trajectory to improve the position of the needle-like medical tool with navigation software 116. At the same time, with the latest CT image, the physician finds the dislocation of the target, skin entry point and the orientation localizer 1 and updates the registered position and orientation of the orientation localizer 1. Thus, the physician can conduct the device-to-image registration with the latest CT images. By updating the device-to-image registration, the physician can reduce discrepancy of the actual geometrical relationship between the orientation localizer 1 and the target. Specifically, since the orientation localizer 1 is mounted on the patient and can move with the patient body together, the update of the device-to-image registration can effectively compensate rigid dislocation of the patient from the older CT images.

With updated plane of the trajectory and the device-to-image registration, the physician can perform another attempt of the insertion with the same steps as in the first attempt.

In step S1212, if the position of the inserted needle-like medical tool is checked and the physician is satisfied with the results (Yes in Step S1212), flow continues to Step S1213. In Step S1213, a determination is made as to whether insertion of another needle-like medical tool is needed. If insertion of another needle-like medical tool is needed (Yes in Step S1213) flow returns back to Step S1205. If insertion of another needle-like medical tool is not needed (No in Step S1213) flow is complete.

Figure 13:
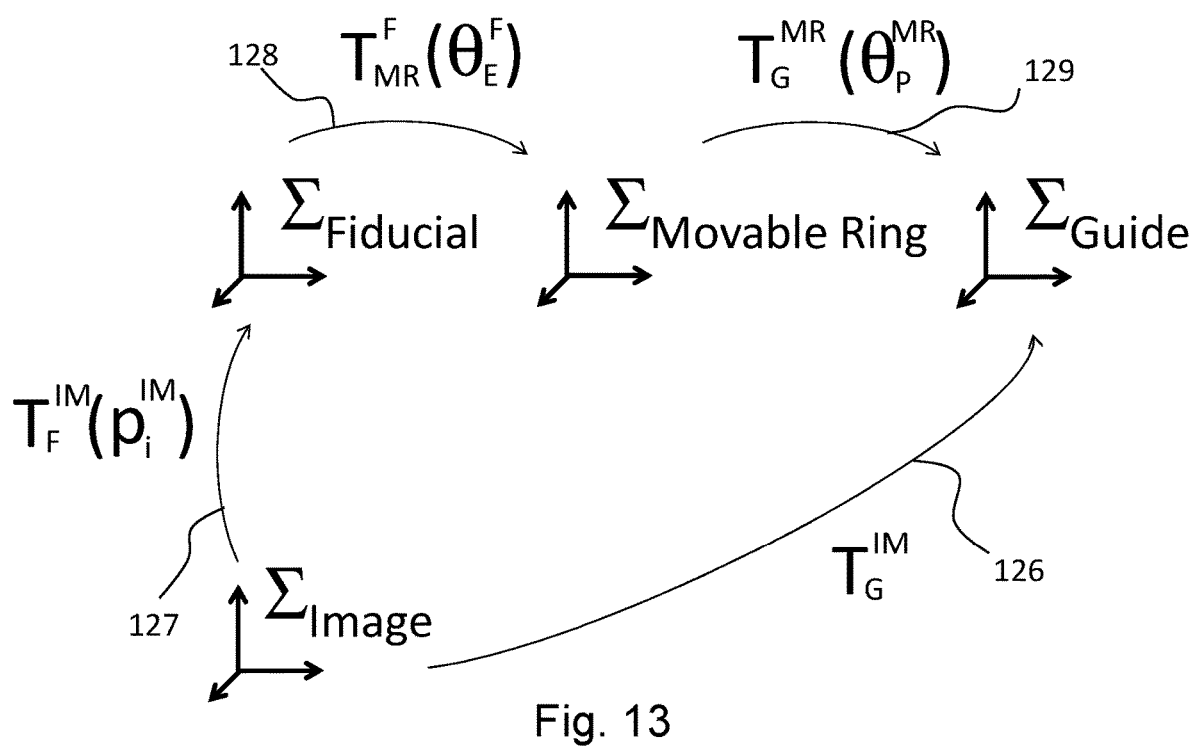
FIG. 13 is a schematic illustration of the transformation of local coordinates in device-to-image registration according an embodiment of the present disclosure.

FIG. 13 is a schematic illustration of the transformation of local coordinates to explaining the device-to-image registration as described in Step S1206 of FIG. 12. Sigma $\Sigma$ signifies a local coordinate according to subscripts. In the device-to-image registration, these local coordinates need to be handled. The first is the coordinate in the medical images $\Sigma_{image}$. This is a fundamental coordinate to express the plane of the trajectory, the targets and the skin entry point in the navigation software 116. Also, the physician correlates this coordinate of the patient in the physical world. The second one is the coordinate of the fiducial markers 121, i.e. the coordinate of the stable ring 10. The third one is the coordinate of the rotatable ring 9, which rotates with the rotatable ring 9 against the stable ring 10 by the angular position of the rotatable ring 9 ($\theta_E^F$). The fourth one is the coordinate for guidance of the needle-like medical tool. In an exemplary embodiment of the present disclosure, one axis of this coordinate is along the target trajectory. Also, one of the other axes is on the insertion-plane indicator 8. Therefore, this coordinate can rotate along the angular reference marks 30 depending on the target insertion angle of $\theta_P^{MR}$ on the insertion-plane indicator 8.

T signifies coordinate transformation, which is a 4 by 4 homogeneous transformation matrix. Superscript with T signifies a base coordinate. Also, subscript with T signifies an objective coordinate for the transformation. The coordinate transformation can be expressed with a homogeneous transformation matrix for three-dimensional space, which includes a four-by-four matrix to define the geometrical relationship between two coordinates.

The four transformations 126, 127, 128 and 129 can be defined among the four local coordinates. The goal of the device-to-image registration is to establish the following equation among the four transformations 126, 127, 128 and 129.

$$T_G^{IM}(p_i^{IM}) T_{MR}^{F}(\theta_E^F) T_G^{MR}(\theta_P^{MR}) \qquad \text{eq. (1)}$$

Where, $T_G^{IM}$ is a transformation to the coordinate for guidance of the needle-like medical tool based on the coordinate in the medical images, $T_F^{IM}(p_i^{IM})$ is a transformation to the coordinate of the fiducial markers (transformation 127) from the coordinate of the medical images, $p_i^{IM}$ is a set of the position vectors of all fiducial markers on the coordinate of the medical image, $T_{MR}^{F}(\theta_E^F)$ is a transformation to the coordinate of the movable ring (transformation 128), $\theta_E^F$ is an angular position of the rotatable ring 9 based on the coordinate of the fiducial markers, $T_G^{MR}(\theta_P^{MR})$ is a transformation to the coordinate for guidance of the needle-like medical tool from the coordinate of the movable ring (transformation 129), $O_P^{MR}$ is insertion angle on the Insertion-plane indicator 8 based on the coordinate of the movable ring.

In equation 1, the navigation software 116 can determine the target values of the device parameters of the angular position of the rotatable ring 9 ($\theta_E^F$) and insertion angle on the insertion-plane indicator 8 ($\theta_E^F$) with the specific position of the base plate, i.e. the position vectors of the fiducial markers at the actual position $p_i^{IM}$, from the target trajectory.

$T_G^{IM}$ of equation 1 is determined by navigation software 116 with the two position vectors of the skin entry point and the target based on the coordinate of the medical images. In Step S1002 of FIG. 10, when the physician defines the skin entry point and the target in the CT image, the navigation software 116 can compute this transformation with defined positions in the CT image.

The parameters $p_i^{IM}$ are determined, when the navigation software 116 gets the positions of fiducial markers 121A, 121B, 121C and 121D in the CT images. Therefore, if the navigation software 116 knows the matrix forms of $T_F^{IM}(p_i^{IM})$, $T_{MR}^{F}(\theta_E^F)$, $T_G^{MR}(\theta_P^{MR})$, the navigation software 116 can derive $\theta_E^F$, $\theta_P^{MR}$ from the plan of the trajectory.

The matrix forms of $T_F^{IM}(p_i^{IM})$, $T_{MR}^{F}(\theta_E^F)$, $T_G^{MR}(\theta_P^{MR})$ are defined by the geometrical design of the orientation localizer and the actual assembly errors. The form of $T_F^{IM}(p_i^{IM})$ is dependent on the design of the configuration of the fiducial markers 121, also, $T_{MR}^{F}(\theta_E^F)$ is defined by the geometrical (mechanical) design, for example the size of each components, position of the movable ring on the base plate and so on, and $T_G^{MR}(\theta_P^{MR})$ is defined by the design of the guide part 109. When the orientation localizer gets the design change, the forms of the transformation also need to be updated. The navigation software 116 always needs to apply the matrix forms of these transformations corresponding to the actual orientation localizer that the physician is using for the intervention.

To keep and guarantee this correspondence between the forms of transformations 127, 128, 129 and the actual orientation localizer that the physician is using, the orientation localizer 1 includes the device information on the forms of transformations 127, 128, 129 in the memory unit 111. The navigation software 116 asks the microcontroller 110 of the device information on the forms of the transformations 127, 128, 129, and establishes the equation 1 with the parameters.

Since the correspondence between the transformations 127, 128, 129 and the actual orientation localizer is established only on the orientation localizer side, the navigation software 116 does not need to be updated and prepare the dedicated device tables. The navigation software 116 can ask the microcontroller 110 of the device information as one universal action for different design and individual of the orientation localizer.

Also, with equation 1, the navigation software 116 can display the cross sectional images on the real-time position of the insertion-plane indicator 8. The navigation software 116 can apply the real-time angular position of the rotatable ring 9 measured by the rotary encoder 104 to $\theta_E^F$ in the transformation 28, and synthesis the cross sectional images on the insertion-plane indicator 8. This cross sectional images help the physician to confirm a critical anatomy surrounding the target, the targets themselves and the treatment area around the target, for example an ablation area, intuitively.

Figure 14:
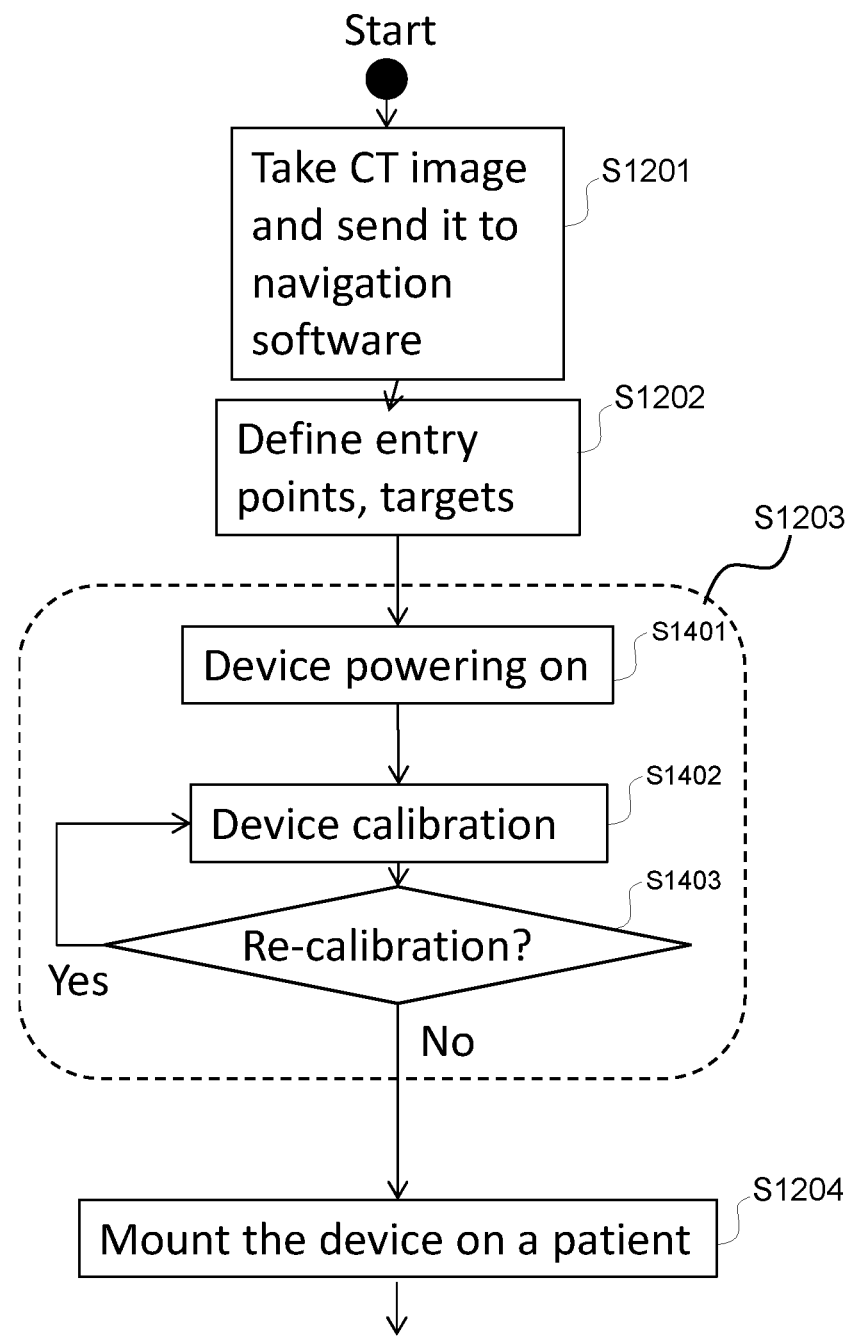
FIG. 14 is an extracted flowchart of FIG. 12 detailing the sub steps for device set up according an embodiment of the present disclosure.

FIG. 14 is an extracted flowchart of FIG. 12 detailing the sub steps for device set up described in Step S1203 for embodiments with the rotary encoder 4 measuring incremental angular position and absolute angular position respectively.

The device set up in Step S1203 in FIG. 10 includes the sub steps of device powering on S1401, device calibration S1402 and confirmation step for the calibration S1403. First, in Step S1401 the physician powers the orientation localizer 1 on. Upon power up, the rotary encoder 104 with the incremental angle measurement does not define the correct angular position of zero. As such, in Step S1402 the physician needs to perform device calibration to establish the correct angular position of zero. This is done with manual alignment of the rotatable ring 9 to the mechanical reference for the correct zero position. With this position established, the physician can teach the correct angular position of zero to the medical guidance system 100.

After the device calibration, in Step S1403 the physician confirms whether a re-calibration is required, and decides whether to proceed to mounting the device on the patient in Step S1204 of FIG. 12. If re-calibration is necessary (Yes in Step S1203) flow returns to Step S1403 to calibrate. If no re-calibration is needed (No in Step S1403) flow proceeds to Step S1204 and the device in mounted on the patient.

These device setting-up steps are required for all devices used for intervention and when the physician needs to turn the orientation localizer 1 off. For example, in instances where the medical guidance system is restarted, these steps are also required. In this case, since the determination for re-calibration is not required (No in Step S1403), the medical guidance system with the rotary encoder 104 to measure absolute angles, can reduce a risk of human-factor errors and the mental load to use the system.

While the present disclosure has been described with reference to exemplary embodiments, it is to be understood that the invention is not limited to the disclosed exemplary embodiments. The scope of the following claims is to be accorded the broadest interpretation to encompass all modifications, equivalent structures and functions.

What is claimed is:

1. A medical guidance system comprising:
an orientation localizer including a plurality of fiducial markers and having a localized plane, wherein the orientation localizer is mountable at a skin entry point on a patient; and
a computer operatively connected to an image display and configured to:
acquire a plurality of computed tomography (CT) medical images of the patient with the orientation localizer mounted on the patient;
identify at least one CT medical image from among the plurality of CT medical images on which the orientation localizer having the localized plane is shown,
register a position and orientation of the orientation localizer with the at least one CT medical image by matching a known layout of the fiducial markers to at least one fiducial marker or to a center of the fiducial markers shown in the at least one CT medical image,
compute, based on the at least one CT medical image on which the orientation localizer is shown, a cross sectional image which is parallel to the localized plane,
determine, based on the cross sectional image, an insertion plane perpendicular to the localized plane and an insertion trajectory at an angle to the localized plane; and
display, on the image display, the at least one cross sectional image on the localized plane and/or the insertion trajectory on the insertion plane,
wherein the orientation localizer guides a needle-like medical tool through the skin entry point to a target position inside the patient according to the insertion trajectory,
wherein the orientation localizer is integrated within a rotatable body which is mountable on the patient, and the rotatable body has a touchscreen interface configured for operation by a user,
wherein the orientation localizer includes light emitting diodes (LEDs) arrayed along a surface of the rotatable body, and one or more of the LEDs light to indicate the insertion plane, and
wherein the touchscreen interface is configured to receive input from the user to change the position and indicate the insertion plane on the orientation localizer.

2. The medical guidance system according to claim 1, wherein the orientation localizer includes angular scales that are arrayed on the orientation localizer and that indicate an angular position of the insertion plane with respect to a reference point on the localized plane, and
wherein the computer determines a target angular scale corresponding to the insertion plane displayed on the image display, and displays the target angular scale together with the localized plane.

3. The medical guidance system according to claim 1, wherein the orientation localizer includes a stable body which includes the plurality of fiducial markers, and the rotatable body which includes an insertion-plane indicator and a rotary encoder,
wherein the orientation localizer is connected to the computer and exchanges encoder data of the angular position of the insertion-plane indicator, and
wherein the computer determines the cross sectional image of an anatomy of the patient based on the insertion plane corresponding to the angular position of the insertion-plane indicator.

4. The medical guidance system according to claim 1, wherein the computer determines information about a planned insertion angle to insert the needle-like medical tool from the localized plane on the insertion plane, and
wherein the computer sends the information about the planned insertion angle to the image display.

5. The medical guidance system according to claim 1, wherein the orientation localizer has an adhesive backing to adhere to the patient.

6. The medical guidance system according to claim 3, wherein the orientation localizer includes an external display unit communicatively-coupled to the rotary encoder via an external cable to display information about the orientation localizer.

7. The medical guidance system according to claim 3, wherein the orientation localizer includes a fixed display unit communicatively-coupled to the rotary encoder via a bus to display information about the orientation localizer.

8. A computer-implemented medical guidance method comprising:
    indicating a skin entry point on a patient, by mounting on the patient an orientation localizer including a plurality of fiducial markers and having a localized plane;
    acquiring a plurality of computed tomography (CT) medical images of the patient with the orientation localizer mounted on the patient;
    identifying at least one CT medical image from among the plurality of CT medical images on which the orientation localizer having the localized plane is shown;
    registering a position and orientation of the orientation localizer with the at least one CT medical image by matching a known layout of the fiducial markers to at least one fiducial marker or to a center of the fiducial markers shown in the at least one CT medical image;
    computing, based on the at least one CT medical image on which the orientation localizer is shown, a cross sectional image which is parallel to the localized plane,
    determining, based on the cross sectional image, an insertion plane perpendicular to the localized plane and an insertion trajectory at an angle to the localized plane;
    displaying, on an image display, the at least one cross sectional image on the localized plane and/or the insertion trajectory on the insertion plane, and
    guiding a needle-like medical tool with the orientation localizer through the skin entry point to a target position inside the patient according to the insertion trajectory,
    wherein the orientation localizer includes a stable body which includes the plurality of fiducial markers, and a rotatable body which includes an insertion-plane indicator, and a rotary encoder,
    wherein the method further comprises exchanging, between the orientation localizer and the rotary encoder, encoder data indicative of an angular position of the insertion-plane indicator, and
    wherein the computing the cross sectional image includes computing a cross sectional image of an anatomy of the patient based on the insertion plane corresponding to the angular position of the insertion-plane indicator.

9. The medical guidance method according to claim 8, further comprising:
    arranging angular scales on the orientation localizer so as to indicate an angular position of the insertion plane with respect to a reference point on the localized plane;
    computing a target angular scale corresponding to the insertion plane displayed on the image display; and
    displaying, on the image display, the target angular scale together with the localized plane.

10. The medical guidance method according to claim 8, further comprising:
    determining information about a planned insertion angle to insert the needle-like medical tool from the localized plane along the insertion plane, and
    sending the information about the planned insertion angle to the image display.

11. The medical guidance method according to claim 8,
    wherein the orientation localizer is integrated within the rotatable body which is mountable on the patient, and the rotatable body includes a touchscreen interface configured for operation by a user,
    wherein the orientation localizer includes light emitting diodes (LEDs) arrayed along a surface of the rotatable body such that one or more of the LEDs light to indicate the insertion plane, and
    wherein the method further comprises receiving input from the user through the touchscreen interface to change the position of and indicate the insertion plane on the orientation localizer.

12. The medical guidance method according to claim 8, further comprising adhering the orientation localizer to the patient, wherein the orientation localizer has an adhesive backing to adhere to the patient.

13. The medical guidance method according to claim 8,
    wherein the orientation localizer includes an external display unit communicatively-coupled to the rotary encoder via an external cable, and
    wherein the method further comprises displaying information about the orientation localizer on the external display unit.

14. The medical guidance system according to claim 8, displaying information about the orientation localizer,
    wherein the orientation localizer includes a fixed display unit communicatively-coupled to the rotary encoder via a bus, and
    wherein the method further comprises displaying information about the orientation localizer on the fixed display unit.

15. A medical guidance system comprising:
    a guidance device configured to guide a needle-like medical tool from an insertion point to a target along an intended trajectory within a patient; and
    a computer configured to acquire computed tomography (CT) medical images of the patient with the guidance device mounted on the patient, and display the intended trajectory together with one or more of the CT medical images,
    wherein the guidance device includes,
        a base plate including a base-plate opening, and a bottom surface configured to be mounted to the patient,
        a movable ring that attaches to the base plate, including a movable-ring opening aligned to the base-plate opening to form a main opening providing access to the patient,
        a guidance part mounted on the movable ring to guide the needle-like medical tool through the main opening, and
        a rotary encoder including:
            a rotary scale mounted on the movable ring,
            a sensor head mounted on the base plate,
            a sensor circuit board connected to the sensor head, and configured to compute an angular position of the rotary scale by processing sensed signals from the sensor head,
        fiducial markers mounted on the base plate and configured to be visible in the CT medical images, and
        a circuit box including:
            a memory unit storing device information to define a geometrical relation between coordinates of the rotary encoder and coordinates of the fiducial markers, a microcontroller connected to the memory unit and to the sensor circuit board, and configured to communicate with the computer, wherein the computer calculates a geometry of the fiducial markers shown in the acquired CT medical images based on coordinates of the acquired CT medical images, and wherein the computer or the microcontroller computes a coordinate transformation of the guidance device with respect to the coordinates of the CT medical images by using the device information in the memory unit and the geometry of the fiducial markers calculated by the computer.

16. The medical guidance system according to claim 15, wherein the rotary encoder is configured to measure an absolute angular position of the rotary scale.

17. The medical guidance system according to claim 15, wherein the microcontroller is configured to send the device information to the computer, and wherein the computer computes the coordinate transformation of the guidance device with respect to the coordinates of the CT medical images by using the device information in the memory unit and the geometry of the fiducial markers calculated by the computer.

18. The medical guidance system according to claim 15, wherein the circuit box includes a wireless communication unit and a battery to power the guidance device, and wherein the circuit box wirelessly communicates with the computer by using the wireless communication unit.

19. The medical guidance system according to claim 15, wherein the circuit box is mounted on the base plate.

20. The medical guidance system according to claim 15, wherein the movable ring is rotatably attached to the base plate.

* * * * *